(12) United States Patent
Dorronsoro Díaz et al.

(10) Patent No.: US 9,808,339 B2
(45) Date of Patent: Nov. 7, 2017

(54) INTRAOCULAR LENS WITH ACCOMMODATION CAPACITY

(71) Applicant: CONSEJO SUPERIOR DE INVESTIGACIONES CIENTÍFICAS, Madrid (ES)

(72) Inventors: Carlos Dorronsoro Díaz, Madrid (ES); Nicolás Alejandre Alba, Madrid (ES); Nandor Bekesi, Madrid (ES); Susana Marcos Celestino, Madrid (ES)

(73) Assignee: CONSEJO SUPERIOR DE INVESTIGACIONES CIENTÍFICAS, Madrid (ES)

( * ) Notice: Subject to any disclaimer, the term of this patent is extended or adjusted under 35 U.S.C. 154(b) by 0 days.

(21) Appl. No.: 15/024,245

(22) PCT Filed: Sep. 24, 2014

(86) PCT No.: PCT/EP2014/070419
§ 371 (c)(1),
(2) Date: Mar. 24, 2016

(87) PCT Pub. No.: WO2015/044235
PCT Pub. Date: Apr. 2, 2015

(65) Prior Publication Data
US 2016/0220351 A1    Aug. 4, 2016

(30) Foreign Application Priority Data
Sep. 24, 2013 (EP) ..................... 13382367

(51) Int. Cl.
*A61F 2/16* (2006.01)
(52) U.S. Cl.
CPC .......... *A61F 2/1635* (2013.01); *A61F 2/1624* (2013.01); *A61F 2/1648* (2013.01); *A61F 2002/1682* (2015.04)

(58) Field of Classification Search
CPC .... A61F 2/1613; A61F 2/1624; A61F 2/1635; A61F 2/1648; A61F 2002/1682
See application file for complete search history.

(56) References Cited

U.S. PATENT DOCUMENTS

| 2003/0109926 A1 | 6/2003 | Portney |
| 2004/0106993 A1 | 6/2004 | Portney |
| 2009/0125106 A1 | 5/2009 | Weinschenk, III et al. |

FOREIGN PATENT DOCUMENTS

WO    WO 2013/126986    9/2013

OTHER PUBLICATIONS

European Patent Office, PCT/EP2014/070419, European Search Report and Written Opinion of the International Searching Authority, dated Dec. 8, 2014, 7 pages.

*Primary Examiner* — Howie Matthews

(57) ABSTRACT

Intraocular lens with accommodation capacity comprising a first optical member (1) having a dynamic optical power, to which a second optical member (2) with a fixed optical power is affixed, in such a manner that at least a central part of each of one of one of the curved surfaces (2a, 2b) of the second optical member (2) and of at least one of the surfaces (1a, 1b) of the first optical member (1) are in contact with each other, the second optical member (2) and the first optical member (1) providing a joint optical power which is variable between a condition of minimum optical power corresponding to a condition of disaccommodation and a condition maximum optical power corresponding to a condition of accommodation, and the first optical member and an anchoring system (3) being designed to change the curvature of at least one of the surfaces (1a, 1b) of the first optical element (1) progressively between a maximum curvature corresponding to the condition of accommodation in response to a minimum effective traction force of the ciliary muscle received through the anchoring system (3), and a (Continued)

maximum effective traction force of the ciliary muscle received by the anchoring system (3).

14 Claims, 6 Drawing Sheets

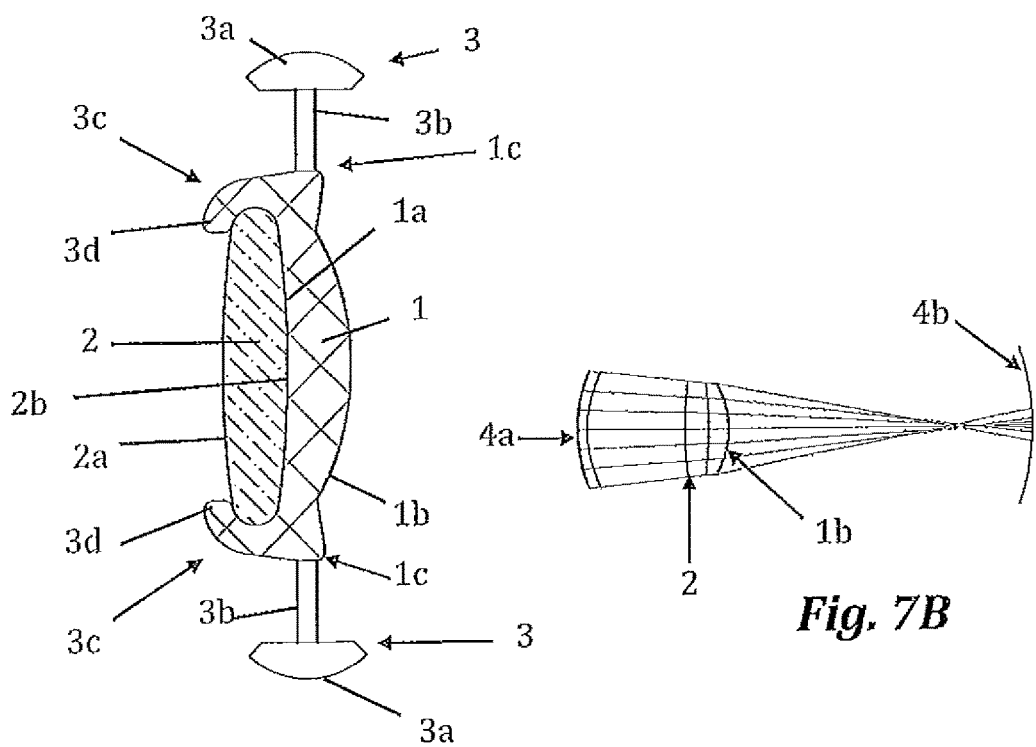
Fig. 7A
Fig. 7B
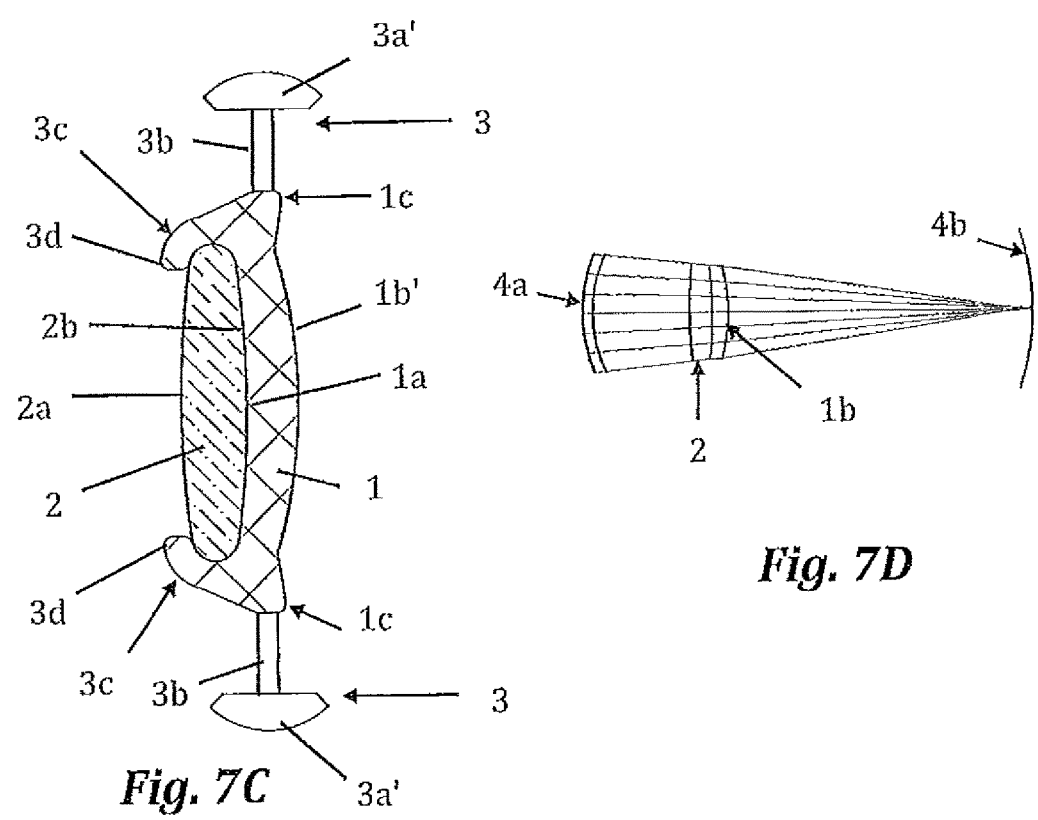
Fig. 7C
Fig. 7D

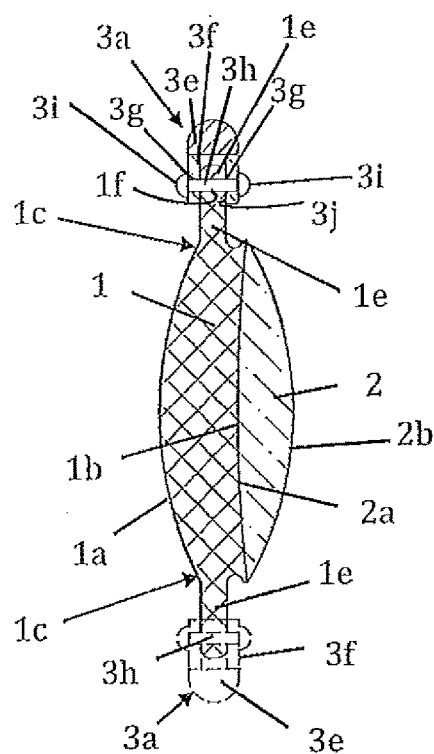
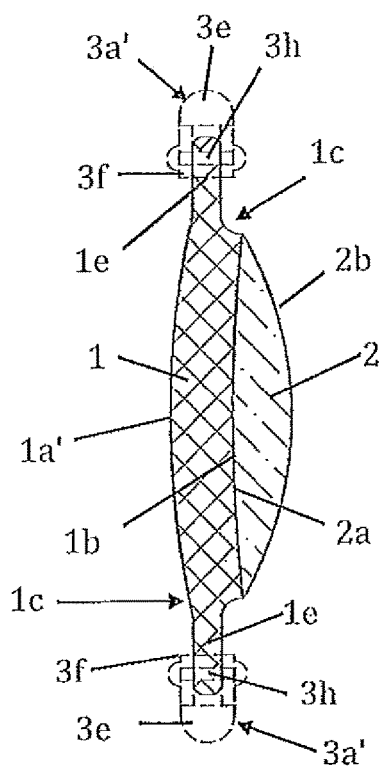
Fig. 8A
Fig. 8B
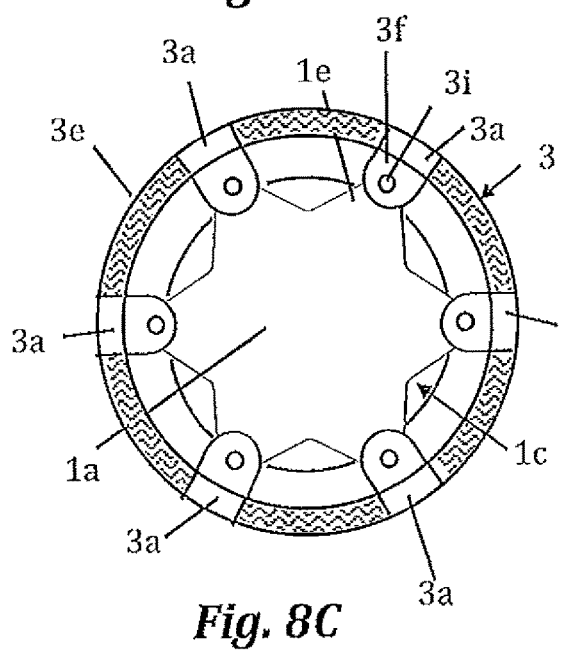
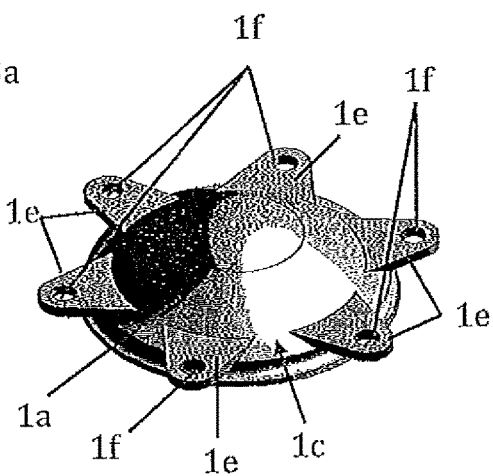
Fig. 8C
Fig. 8D

INTRAOCULAR LENS WITH ACCOMMODATION CAPACITY

TECHNICAL FIELD OF THE INVENTION

The present invention is comprised within the field of ophthalmic correction of presbyopia and, in particular, in the area of ophthalmic intraocular lenses, which are implanted inside the eye for such correction.

BACKGROUND OF THE INVENTION

The young eye has the capability of focusing far and near objects, a capacity known as accommodation. The human crystalline lens, the second of the lenses, behind the cornea, which forms the eye optical system, responds to an accommodative stimulus by changing its shape in order to change its dioptric power. The ciliary muscle transmits a primarily equatorial force through its zonular fibers to the capsular bag (the outer membrane of the crystalline lens). When the crystalline lens is disaccommodated, the ciliary muscle relaxes, stretching the zonular fibres which in turn stretch the capsular bag, and flatten the surfaces of the crystalline lens. When the crystalline lens is accommodated, the ciliary muscle contracts relaxing the zonular fibers, thereby allowing the capsular bag to adopt a more curved shape. With aging the crystalline lens progressively loses elasticity and thus a loss of the accommodating capacity (a condition known as presbyopia). At a more advanced stage of aging, the crystalline lens moreover loses transparency (a condition known as cataract) making necessary an exchange of the opacified crystalline lens by an artificial intraocular lens by means of cataract surgery.

In current cataract surgery, a window is made in the capsular bag (capsulorrhexis) either by mechanical means or, since more recently, with femtosecond laser. The content of the crystalline lens (previously fractured either by phacoemulsification or, since more recently, by laser) is extracted through the capsulorrhexis, by aspiration. The intraocular lens is implanted, generally folded, through a small corneal incision, into the capsular bag where it unfolds. Generally the intraocular lens is stabilized in the capsular bag by means of plates or curved prolongations, called haptics, which tighten the equatorial region of the capsular bag.

Today the more frequently implanted lenses are monofocal. Pseudophakic patients and presbyopic patients (who are implanted with monofocal intraocular lenses) only perceive one focus plane, which makes it necessary to resort to the use of near vision, bifocal or progressive spectacles (using an optical correction with a different power for each eye), or multifocal contact lenses to provide near vision. None of these solutions offers a satisfactory correction of presbyopia because the dynamic capacity of accommodation of the young eye is not restored.

During the last years a great number efforts have been invested in the replacement of the rigid or opacified crystalline lens by a filler material which may be a flexible polymer or a gel, with or without membrane coating, injected in the emptied capsular bag, as described for example in patent application WO2012/126053. This kind of approach to restore accommodation depends on the capsular integrity, its transparency as well as the stability of its mechanical properties. These attempts have been unsuccessful due to capsular fibrosis which usually occurs in the months following cataract surgery due to proliferation and transdifferentiation of the epithelial cells of the crystalline lens, and which results in a dramatic change of the mechanical properties of the capsular bag which loses both its elasticity and transparency. In contrast to what happens with conventional intraocular lenses where the capsule is not necessary for correct functioning of the intraocular lens, and transparency can thus be returned to the eye by making an opening in the opacified posterior capsular bag, which is usually done by laser (posterior laser capsulotomy), in the case of capsular bags provided with a filler material, capsular fibrosis has become an insurmountable obstacle where mechanical integrity is indispensable, this causing capsular refilling techniques, at least nowadays, to be clinically unviable.

Furthermore, in the last years numerous accommodating intraocular lenses have been proposed, which are provided with mechanisms that contrarily to monofocal intraocular lenses, with one fix focus plane, aim to dynamically alter the power of the eye. The majority of these designs have failed for not being based on a correct understanding of the accommodating mechanism, being dependent on the integrity of the capsular bag after surgery, not using the available accommodating forces, or limitations in the design of the operation of the intraocular accommodating lens.

Thus, at present, the only accommodating lens approved by the US Federal Drug Administration (CRYSTALENS, marketed by Bausch and Lomb, NY, USA) is a single optic intraocular lens, with haptics provided with a hinge (Cumming, US20040249456) which provide for a possible axial movement of the optic area of the intraocular lens and thus a change in ocular refraction. Although, nominally, the intraocular lens should move forward in the accommodated state, it has been proved that in many patients the optical lens actually moves backwards in response to an accommodative stimulus. Moreover, a relevant change in refraction would need a forward movement of 1 mm of the intraocular lens in the anterior segment of the eye, which is not achieved in any patient. Another intraocular lens (TETRAFLEX Lenstec, FL, USA) does not use hinges, but its principle is also based on axial displacement. Further, there is at least one accommodating intraocular lens in the market (SYNCHRONY, marketed by Advanced Medical Optics, CA, USA), and other accommodating intraocular lenses proposed in patents which are constituted by two joined lenses linked by some mechanism which transforms accommodating forces into a relative displacement of the two optics with respect to each other so as to provide a change in optical power. The majority of these lenses assume an axial displacement along the optical axis, although some assume a lateral movement based on the Alvarez principle (such as the AKKOLENS of Akkolens International, Netherlands).

One frequent problem identified in many of the proposals regarding accommodating lenses is the lack of connection between the capsular bag and the intraocular lens system which allow adequately transferring the movement of the ciliary muscle to the operating mechanism of the intraocular lens, as described in U.S. Pat. No. 7,150,760B2. Some lenses try to achieve the fastening means of the natural fibrosis occurring at the haptics during the weeks following implantation of the intraocular lens, as described in US2005/0119741A1. Several haptics' devices and designs have been proposed to favor said fibrosis process, as for example ring shaped collars as those proposed by Cummings (US2001/0005794A1); the so called zonular capture haptic which favors fusion of the capsular bag to the haptics using the natural fibrosis process (Beer, in US2011/0307058A1); a porous or perforated plate as a retaining structure for an accommodating lens (Glasser and Coleman, in US2008/

0221676), or contact plates along the equatorial region (separating anterior and posterior capsule) with a relatively large contact surface to promote cell and fiber proliferation in the anchoring area of the intraocular lens to the capsular bag (Lang, in U.S. Pat. No. 6,660,035B1). Depending on the natural fibrosis in respect of the mechanism for connecting the intraocular lens and the capsular bag has several drawbacks, such as the duration of this process (weeks), the relative uncertainty of the symmetry, and the result of the final anchorage. Some authors have proposed mechanical anchorages of the intraocular lens to the edge of the capsulorrhexis using clasps, brackets or pins (Peng US2003/0204254A1) or bioadhesives (Reisin, US2011/0029074A1; Thomson WO1996/035398A1).

The human crystalline lens changes its shape while accommodating, so that an intraocular lens design based on the surface shape change would mimic the natural accommodating mechanism more closely in contrast to axially displacing lenses. Several patents propose multi-mechanism designs which simultaneously displace and deform (Paul, in US2004/0127984A1). Several proposals propose global general concepts of an intraocular lens, operating by one or two optics moving axially or by means of changes in curvature (Cumming, en US2008/0269887).

Several designs propose intraocular lenses conceived to change curvature in response to an accommodating force. However, several of these designs fail regarding the operation principle they are based on. For example the "Nulens" of the company (Nulens Ltd., Israel, consists of two plates separated by a viscoelastic material, the anterior one of which has an aperture. The mechanism of this intraocular lens assumes that the capsular bag (emptied from its crystalline content) exerts o force upon the posterior plate, which should become a piston approaching both plates in such a way that the elastic polymer bulges through the anterior aperture thus forming a more curved intraocular lens. It has been shown that, completely unlike the natural crystalline lens the greatest curvature is achieved in the disaccommodated condition. Other proposals consider hinge mechanisms comprising one or two deformable lenses, although they consider that the mechanism by which the intraocular lens increases its dioptric power, is based on an increase of the pressure in the vitreous cavity. (Cummings, in US2008/0269887A1). Other lenses (Woods, in U.S. Pat. No. 6,217,612B1) define an intraocular lens constituted of polymer material with a elastic memory, the concept of which is interesting inasmuch they would have the shape of maximum accommodation in the absence of zonular tension (as it happens in the young human eye). However, this intraocular lens depends critically on the general integrity of the capsular bag because the pressure exerted by the walls of the capsular bag upon the intraocular lens.

Other accommodating intraocular lenses proposing the modification of the dioptric power of the intraocular lens by a change of the curvature of its surfaces, are those based on fluids, generally covered by a membrane. In general, said lenses design have complex designs, as they require, among other elements, the presence of reservoirs, valves, systems for evacuation and circulation of the fluid. Besides, the principle of transmitting the forces of the ciliary muscle to these lenses is not always adequate. One of the first proposed fluidic lenses (Schachar, in U.S. Pat. No. 4,373,218A) suggests the use of electrodes and microprocessors to control the forces exerted upon the lens. Another document (Chawdhary, US2007/0129798A1) proposes a deformable fluidic device, generally in combination with a rigid intraocular lens implanted in the ciliary sulcus with the purpose of being in response to the forces of the ciliary muscle. The direct coupling of the lens to the ciliary muscle seems to be little viable in practice due to the textures and consistency of said tissue. One of the most advanced fluidic lenses is the one developed by Powervision, CA, which has already been implanted in patients. This is an intraocular lens with microchannels for fluid circulation and reservoirs placed in the haptics. One of the limitations of this intraocular lens is its dependency on the size of the capsular bag and the integrity thereof, for its functioning.

Regarding several lenses of a deformable type, the advantages of one fixed and one deformable have been highlighted. The fixed component would provide the correction of the refractive error of the patient while the deformable component would provide the dioptric change needed to accommodate at several distances. Turley (U.S. Pat. No. 4,892,543B1) proposed an intraocular lens with two components (of fixed and variable power respectively) emphasizing that the first optical component would still be working even if the second component failed or was destroyed providing a security feature to the intraocular lens. One limitation of this proposal is its implantation in contact with the ciliary muscle. Thomson (WO1996/035398A1) proposed an intraocular lens with a fixed component and another deformable one, with the deformable part connected to an anchoring system of the intraocular lens and to the capsular bag. However, said anchoring is limited to a mechanical or glued connection of only the border of the capsulorrhexis therefore wasting the forces applied directly equatorially to the capsular bag. Brady (US2007/0078515) proposed an accommodating intraocular lens with two components, one fixed and one deformable. In this case, the deformation occurred due to pressure and contact between the two components of the intraocular lens. In a later patent, Brady (U.S. Pat. No. 7,713,299B2) presents a haptic system for anchorage of the intraocular lens and the capsular bag adapted for accommodating intraocular lenses with two components: one deformable and one fixed. Weinschenck (U.S. Pat. No. 6,645,246B1) proposed an intraocular lens with two components, one fixed and one deformable; the rigid part constitutes the core of the accommodating intraocular lens and the flexible part is linked to the capsule by a rigid force transmission assembly.

However none of the proposed or available accommodating intraocular lenses provides the eye with the accommodating capacity of the young crystalline lens in an effective manner.

DESCRIPTION OF THE INVENTION

It is the object of the present invention to overcome the inconveniences of prior or by mean of an ophthalmic intraocular lens with accommodation capacity, comprising an optical power system comprising a first optical member with dynamic optical power which comprises two surfaces respectively corresponding to a an anterior surface and a posterior surface, at least one of which has a curvature capable of becoming deformed elastically in response to traction forces of the ciliary muscle of the eye, an equatorial region about the surfaces, and at least one deformable preformed material, as well as a second optical member with a fixed optical power having a curved anterior side and a posterior curved side, the second optical member being associated to the first optical member in such a manner that the first optical member and the second optical member jointly have a joint optical power determined by the fixed optical power of the second optical member and the dynamic optical power of the first optical member, an anchoring system to anchor the first optical member to at least a portion of the capsular bag of the crystalline lens of the eye, to directly transmit traction forces generated by the ciliary muscle and transmitted to the capsular bag through zonular fibers to the first optical member, the capsular bag comprising, in its natural state, an anterior capsule, a posterior capsule and an equatorial capsule, the anchoring system being selected from mechanical fastening systems, biocompatible adhesive systems, microstructure systems fostering capsular fibrosis, and combinations thereof, wherein the second optical member is joined to the first optical member in such a manner, that at least respective central portions of one of the curved sides of the second optical member and at least one of the surfaces of the first optical member are in contact with each other;

the joint optical power is variable between a condition of minimum optical power corresponding to a condition of disaccommodation where the intraocular lens is capable of focusing the eye to a far vision distance, and a condition of accommodation where the intraocular lens is capable of focusing the eye to a reading distance;

the first optical member and the anchoring system are designed to change the curvature of at least one of the surfaces of the first optical member progressively between a maximum curvature corresponding to the condition of maximum accommodation in response to a minimum effective traction force of the ciliary muscle received by the anchoring system, and a minimum curvature corresponding to the condition of disaccommodation in response to a maximum effective traction force of the ciliary muscle received by the anchoring system.

The optical members are optical lens or lens-type members or elements producing the effects of a lens.

The term "anchoring points" as used in this description and its appended claims is not limited to small extensions but also includes zones or regions where the intraocular lens is anchored to the capsular bag of the crystalline lens of the eye.

The term "effictive" as here employed means that the increase or decrease of the traction forces of the ciliary muscle only results in changes of the surface or surfaces of the first optical member until disaccommodation of the eye takes place resulting in a far vision distance when the ciliary muscle relaxes, or contrarily, until accommodation of the eye takes place resulting in reading vision distance when the ciliary muscle contracts. Once these maximum or minimum traction forces have been surpassed, no change of the curvature of the first optical member takes place which might result in a greater disaccommodation or in a greater accommodation. This may be achieved, for instance, by limiting the maximum and minimum curvatures of the preform of the first optical member and/or by limiting the capacity of transmission of the traction forces by the anchoring system to a range of maximum and minimum forces.

The functioning of this intraocular lens allows that, in its accommodated position when the traction forces exerted on the anchoring points of the anchoring system to the capsule of the crystalline lens decrease, the first optical member achieves its preform maximum curvature and its maximum optical power. When combined in this accommodated configuration with the second optical member, the eye is enabled to focus nearby objects. On the other hand, in the disaccommodated eye, when the traction forces exerted on the anchoring system increase and its anchoring points to the capsule of the crystalline lens adopt their most separated positions, the traction forces as exerted make the first optical member acquire a position of minimum curvature and minimum power. The second optical member does not change but, in combination with the first optical member in its disaccommodated condition, it is now focused on distant objects. Therefore, the transition between the accommodated configuration and the disaccommodated configuration takes place in a progressive manner and there is thus a continuous range of optical powers and vision distances.

The technical solution as proposed for the intraocular lens with accommodation capacity, which is the object of this invention, is new with respect to existing approaches and has important advantages, as unlike other lenses, the proposed particular mechanism of action is based directly on the physiologically-generated forces in the human eye, emulating the performance of a fully functional crystalline lens. This direct transmission of forces is achieved by the anchoring system which directly anchors the first optical member to at least a portion of the capsular bag, with no intermediate mechanisms or elements; i.e., the anchoring system is a direct force transmitter between the capsular bag and the first optical member of the lens, irrespective of whether the anchoring system is a mechanical fastening system, a biocompatible adhesive system, a microstructure system fostering capsular fibrosis, or a combination thereof. Unlike other existing approaches which redistribute the forces generated by the ciliary muscle and/or change their orientation, in the present invention the forces existing in the capsular bag are directly transmitted to the first optical member by the anchoring point fixed to the capsular bag.

Division of optical power into two elements (second optical member and first optical member) allows decoupling the personalized correction of the refractive error and the restoration of accommodation.

According to the invention, the first optical member may be positioned in front of the second optical member such that at least a central portion of the anterior side of the second optical member is in contact with at least a central portion of the posterior surface of the first optical member. Alternatively, the first optical member may be positioned behind the second optical member such that at least a central portion of the posterior side of the second optical member is in contact with a central portion of the anterior surface of the first optical member.

According to another alternative, the first optical member externally surrounds the curved sides of the second optical member, and each of the two curved sides of the second optical member is arranged adjacent to one of the inner surfaces of the first optical member, and at least the central portions of the curved sides of the second optical member are in contact with the central portions of said inner surfaces.

On the other hand and according to another alternative, the first optical member may be located between respective halves of the second optical member. Each half comprises an outer convex portion and an inner concave portion. According to this alternative, the convex portion of one of said halves comprises the anterior curved side of the second optical member, and the convex portion of the other of said halves comprises said posterior curved sided of the second optical member. In this way, the surfaces of the first optical member are arranged adjacent to the inner concave portions of the halves of the second optical member, whilst at least the central portions of the first optical member are in contact with at least the central portions of the respective concave portions of the halves of the second optical member.

The mechanical fastening system may comprise retaining parts to capture and retain tissue of the capsular bag of the crystalline lens, whilst the biocompatible adhesive system may comprise an adhesive substance applicable between the retaining parts and the tissue of the capsular bag. Alternatively or complementarily, the biocompatible adhesive system may comprise at least one adhesive substance selected from adhesive substances which are directly applicable between peripheral material of the first optical member and the tissue of the capsular bag, and adhesive substances which are applicable between portions of the first optical member available between two areas of the tissue of the capsular bag. These adhesive substances may require, or not, mechanical, chemical or luminous activation mechanisms, or combinations of said activation mechanisms.

The anchoring systems may as well comprise a microstructure system promoting capsular fibrosis which comprises a biocompatible material with microstructures which promote capsular fibrosis. The anchoring system may as well comprise a biologically absorbable coating, such as silk or collagen, to cover the microstructures during surgical implantation of the ophthalmic intraocular lens.

Alternatively, the biocompatible adhesive system may be based on the use of processes allowing direct adhesion between the retaining parts and tissue of the capsular bag by means of chemical reactions which may require introduction of a reactant, as well as an activation mechanism selected from mechanical, chemical, thermal and luminous activation mechanisms, or combinations of said activation mechanisms.

Preferably, the intraocular lens according to the present invention comprises a tridimensional structure having a shape designed to emulate the shape of the equatorial capsule of the capsular bag of the crystalline lens, to maintain the anterior capsule spaced from the posterior capsule and to maintain the traction forces of the zonular fibers substantially equal than in the natural eye.

The anchoring system between the first optical member and the capsular bag fixes the intraocular lens in such a manner that it allows both to move jointly. In addition to capturing the forces proceeding from the accommodative system, the anchoring system between the first optical member and the capsular bag of the eye acts as positioning mechanism of the intraocular lens in the inside of the eye, in the same manner as it would be done by the haptics of a conventional monofocal intraocular lens.

There are different possibilities to put the anchoring system between the first optical member and the capsular bag of the crystalline lens of the eye into practice. The different possible embodiments of the anchoring system aim at achieving a balance between providing contact and connection between the capsule of the crystalline lens and the intraocular lens, but at the same time allowing the direct transmission of forces of the capsular bag to the intraocular lens as well as the stability of the intraocular lens. This balance may be achieved by means of uniformly distributing the anchoring points along the equatorial region of the first optical member.

The anchoring system may be selected from sets of discrete anchoring points which are uniformly distributed along the equatorial region of the first optical member and continuous systems which extend along said equatorial region.

In the case of a discrete distribution, a discrete set of more than three anchoring points is preferred, which guarantees a uniform distribution of forces around the equatorial region. It is also desirable to have less than twelve anchoring points so as to prevent unnecessarily complicating the surgery without any benefits.

The anchoring system may be designed to become fixed to at least one side of the capsular bag of the crystalline lens, for example at its anterior side, its posterior side or at both sides of the capsular bag of the crystalline lens.

One of the possible anchoring systems is an adhesive biocompatible system comprising direct bonding between the capsules and bonding surfaces which are part of the anchoring system. These bonding surfaces shall preferably have an extension being such that it facilitates contact and connection between the capsule of the crystalline lens and the anchoring system, but which at the same time allows the transmission of forces and mobility of the intraocular lens. This balance may be achieved by means of the distribution of the bonding points as a discrete set of extensive areas, as for example between 3 and 12, about the equator of the intraocular lens.

Bonding may be based on different mechanisms, among which the use of an adhesive or promotion of bioadherence stands out. The design of the contact surfaces must be appropriate to the bonding mechanism. In the case that a biocompatible adhesive is used, it may preexist as a coating on the contact surfaces. In an alternative or complementary manner, the bonding surfaces may contain a system for applying the adhesive as precharged equatorial or peripheral deposits. Activation or release of the adhesive may be associated to a temperature change or to diffusion after a certain time, or to a physical releasing mechanism which is activated by the deployment of the intraocular lens within the eye during implantation thereof. Activation or release of the adhesive may also depend from the surgeon's action; application of pressure causing the release, injection of the adhesive from outside through channels existing in the intraocular lens, operation of a valve or withdrawal of a seal.

Another possibility for a fixing mechanism of the anchoring system that may be used as an alternative to bonding albeit it may also be used in combination therewith, is a clamp mechanism, this being understood as two parts which one closes upon the other trapping the capsule therebetween. This clamping may be performed without piercing the capsule, by a clip or clasp type mechanism, or by piercing by a staple or rivet type mechanism. Independently of the mechanism, the contact surfaces may be punctiform or extensive, and in the case that they are extensive, they may have a smooth or otherwise shaped surface geometry to increase the grip such as undulations or roughness, of reciprocal fitting or not. Hybrid clamping combinations are also possible, especially microstructures providing a great density of contact points and/or microperforations of the capsules which do not tear the same.

The anchoring system between the first optical member and the capsular bag may use various possibilities among the described fastening mechanisms, as long as the anchoring system directly anchors the first optical member to at least a portion of the capsular bag, without any intermediate mechanisms or elements; i.e., the anchoring system is a direct force transmitter between the capsular bag and the first optical member of the lens.

The accommodative intraocular lens being the object of the invention depends on the correct transmission of forces at the equatorial region of the first optical member but not on the central capsule of the crystalline lens. Differently to the majority of conventional accommodative intraocular solutions, the intraocular lens according to the present invention works equally with and without the anterior or posterior central capsule and is thus fully compatible with capsulotomy processes. As a consequence, the intraocular lens is immune against fibrosis processes and capsular opacification which may be easily treated. It is well known that the zonular fibers do not set only at the capsular equator but also at a region surrounding the equator. If the implantation of the lens is limited to fastening it to the capsular equator as it occurs in the case of conventional haptics of monofocal lenses, a redistribution of the forces among zonular fibers is produced as some fibers increase their tensions and other lose them. This may reduce the effectiveness of the transmission of forces, and overstrain some of the zonular fibers.

In a preferred embodiment of the intraocular lens which is the object of this invention, the fastening system of the intraocular lens forms a tridimensional structure which, at its equatorial region, copies the anatomic shape of the surface of the natural crystalline lens. Thereby, tension becomes distributed among the zonules of the equator and the zonules which are close to the equator, the same as it occurs in the natural accommodative system. As the shape of the equatorial ring is preserved and the tensions of the zonules are being maintained unalterated, a better use of the weak accommodation forces is achieved. Futhermore, tension in the capsule increases and, as the separation between the anterior and posterior capsules is maintained, opacification of the posterior capsule is prevented. Finally, the increase of the contact surfaces between the intraocular lens and the capsules facilitates fastening and the transmission of forces.

The main mechanism of action of the accommodative lens according to the present invention, is the change of the curvature of at least one of the surfaces of the first optical member. However, intentionally or not, axial movements of the lens may occur along with the accommodation. If the volume of the lens moves towards the posterior pole, the eye loses power and the posterior capsules may restrain movement of the lens and its deformation, but medical complications are not anticipated. However, if the volume of the lens moves towards the anterior pole, although the eye increases its power, there is the risk of the iris being contacted, which may cause dispersion of the pigment, closure of the trabecular angle and the possibility of acute glaucoma. Due to all this, in the intraocular lens which is the object of the invention, the haptics of the fastening system are designed in such a manner (by combining the point of insertion of the haptics in the first optical member and the inclination of the haptics with respect to the equatorial plane) that only slight axial movements take place, and favoring an accommodated position which is an anterior one compared to the disaccommodated position, but without reaching to touch the iris.

The first optical member may be made of a single deformable preformed material or, alternatively, comprise a plurality of layers of different deformable preformed materials. Also, the first optical member may comprise one or several layers of deformable preformed material combined with a moldable filler material, or an enveloping layer or membrane which coats a filler material. The enveloping layer or membrane as well as the filler material must be deformable or moldable, although they may or not be preformed.

On the other hand, the first optical member may comprise a composite material with a refraction index gradient such that upon receiving the traction forces, it produces a redistribution of the refraction indices that generates a change in power additional to that produced by the change of the curvature of at least one of its surfaces. The crystalline lens of the eye shows a radial and axial index gradient distribution which, among other advantages, confers to it an increase of the effective power with relatively low refraction indices in its core and its periphery. Although in the crystalline lens of the eye the redistribution of the index gradient turns into a larger rate of change in power for the same change of the surface curvature, it is possible to incorporate index gradient distributions into the first optical member, which produce a change in power which is additional to that produced by the change of the curvature of at least one of its surfaces.

The first optical member of the intraocular lens is a deformable optical member which, in the absence of external forces, tends to adopt a predetermined preform that is stable, known, controllable, and provides the maximal power to the optical member. This tendency may be considered as an internal accommodating force which is similar to that existing naturally in the fully operative crystalline lens before having been affected by presbyopia.

The predetermined preform is designed in such a manner that, in combination with the second optical member, it provides the eye with the near vision focusing distance. As a consequence of the traction force or stretching exerted by the ciliary muscle during the disaccommodation process of the eye, the first optical member has the capacity of responding by a progressive flattening (decrease of the curvature) of at least one of its surfaces, and thus by a decrease of its power providing a clear vision at intermediate distances and, finally, distances corresponding to far vision. Contrarily, when the eye accommodates, the external traction force applied to the lens decreases, and the first optical member progressively increases the curvature of at least one of its surfaces and thus its optical power, until it gets back, completely or partially, to its preform. Thus, the first optical member is able to transform, within a certain range of operation of traction forces as applied, the different forces applied to it into different optical powers which are used by the intraocular lens which is the object of the invention, in order to be able to focus on objects within the range from far to near distances in combination with the second optical member.

So as to make the mechanism viable, the internal accommodation force of the first optical member must necessarily be of a lower magnitude than the traction forces applied by the ciliary muscle when disaccommodating. On the other hand, the internal accommodation force must be sufficiently strong to provide the return to the accommodated position within a short time, ideally in fractions of a second.

The materials used, be them the single deformable material, the enveloping layer or membrane or the filler material, may be compressible or uncompressible. In the case of uncompressible materials, the changes in shape may entail a redistribution of volumes which is to be taken into account during the design. The design of the first optical member may be based on simulation by means of finite element models in which the elastic properties of the materials are considered in order to enable the prediction of the deformation of the surfaces in response to the application of forces.

The shape of the intraocular lens when it rests i.e. the predetermined preform in the complete or partial absence of forces, imposes a limit to accommodation, a maximum curvature of the first optical member and thus a stable near vision distance which is free of fluctuations once the contraction o the muscle above a predetermined level has been achieved.

The far vision focus which is considered one end of the range of accommodation, will be given by an accurate selection of the second optical member to make into combine adequately with the first optic member in the configuration of maximum power. The width of the range of accommodation will be given by the variation of the optical power (in diopters) that the first optical member is able to generate. The other end of the range of accommodation will be the near vision distance which must be stable in order to provide visual comfort to the patient. For this purpose, it must be made to correspond with the natural reading distance of the patient, typically between 20 and 50 cm.

The intraocular lens according to the present invention may be provided with a limiting system which imposes a physical limit to the decrease of the curvature of the first optical member and establishes a minimum of optical power for the intraocular lens, and thus a physical limit to the disaccommodation of the first optical member. Such a limit may be established, for example, by means of stops or retainers to establish a maximum to flattening of the curvature(s) of the surfaces of the first optical member, using a structure which is internal or an external to the deformable surfaces and allows that the traction forces produced by the ciliary muscle when relaxing do not take the first optical member beyond the power corresponding to far vision, as that would cause an excessive decrease of the power thereof which would entail out-of-focus images on the retina. Moreover, including this solution limiting the maximum disaccommodation provides the additional advantage of providing far vision without fluctuations and thus a more comfortable one, similar to what occurs in a monofocal intraocular lens.

Many of known accommodative ophthalmic intraocular lenses aim at the largest possible power range, with an accommodation that varies in a continuous and proportional way to the force applied. Many of the accommadative lenses proposed in patent documents and scientific publications determine a potential range of 10 diopters or more, in the order of the magnitude of the young crystalline lens. However, the inclusion of physical limits to the range of accommodation, be it a limit to accommodation given by the preform of the first optical member corresponding to a close vision or reading distance, or a limit to disaccommodation of the first optical member corresponding to a far vision, represents a novelty that provides various advantages.

The main one of these advantages is providing a comfortable close and far vision and without fluctuations. Thus is due to the fact that the limit positions of the range of powers (far vision distance and reading distance) are the ones which are most frequently used and which are used in a continuous manner. However, distances beyond the infinity or closer to reading distance are rarely used, but they are areas within which the visual system may fall, and which it must get out of by making an overstrain to adjust forces and deformations. Although natural accommodation is sufficiently precise and agile to manage this situation without an appreciable effort, this situation is very different in the case of an implanted artificial lens. The natural accommodation mechanism is difficult to emulate in a precise manner as it is based on forces of a very small magnitude. The whole range of natural optical powers is correlated with an expansion or contraction of the equator of the crystalline lens over only fractions of a millimeter. Already slight imbalances in the control, application or transmission of forces may entail enormous changes in power and serious difficulties in focusing objects at a certain distance. In this scenario, the presence of accommodative or disaccommodative stops, especially if adjustable, secure that oscillations occur within and especially between the limits of useful vision, without unpleasant oscillations outside this range. Furthermore, the presence of the limits of accommodation and disaccommodation makes it much easier to predict the refraction of the intraocular lens once it has been implanted, and thus increases the rate of correctness in the eye's refraction. The high rate of correctness in the refraction up to a point where the vast majority of patients are deprived of the need of wearing spectacles for far vision, is an achievement which has already been attained with monofocal lenses in cataract surgery, and which is difficult to be waived by surgeons and patients. This intraocular lens additionally proposes eliminating the need of near vision spectacles.

Although the physical limit of accommodation is determined by the preform of the first optical member in the absence of forces (or at residual forces), there are different possibilities for putting the physical limit of disaccommodation into practice. It may be based on a structure that limits the maximum separations of arms forming the fastening system which thereby limits the stretching force. One possibility is that this structure is based on a flexible ring or set of arches, which avoids deformation of the intraocular lens beyond the deformation caused by complete stretching of the ring. Based on the same principle of operation, polygons or variations of polygons, or sections thereof may be used. This system may act in terms of the contact points of the intraocular lens with the capsule or in terms of the connection points of the first optical member, or in terms of any other fastening system. Another possibility of putting into practice the physical limit of disaccommodation, is the limitation of the minimum curvature of the surfaces of the first optical member through the limitation of the maximum equatorial expansion. This may be achieved, for example, by means of one or various internal braces along the diameter, or by means of an annular structure which avoids expansion one it has reached a limit. Further to the equatorial intervention, it is possible to achieve an axial physical stop by simply setting a maximum thickness or a minimum curvature that may be supported by the design of the second optical member such that it acts by itself as a stop regarding deformation of the first optical member. The best solution among the numerous possible solutions will depend on the spatial arrangement relative to the elements composing the intraocular lens.

The second optical member in turn is a passive optical element which combines with the first optical member, to provide the joint optical power demanded by the patient's eye to correct the refraction thereof. In combination with the range of powers provided by the first optical member, it provides the patient's eye with a particular range of distances from far to near vision, to thereby correct his/her presbyopia.

Essentially, the second optical member is similar to the optical part of a monofocal intraocular lens, having an optical power that combined with the minimum power of the first optical member, it provides the patient with an adequate refraction for far vision. This member is connected to the rest of the intraocular lens, but forces of the anchoring system to the capsular bag are not directly transmitted thereto. The second optical member may be integrated in a continuous or progressive way with respect to the rest of elements composing the intraocular lens, or may be bonded, fitted or suspended.

In an embodiment of the invention providing desirable characteristics, the second optical member is exchangeable by surgical operation, which thus allows fine adjustment of the far vision refraction and of the position in diopters of the power range of the intraocular lens with accommodative capacity which is the object of the invention.

The second optical member may be designed to provide a physical support structure for the intraocular lens, with respect to which the first optical member and the anchoring system are positioned. Also, the first optical member may be designed to provide the intraocular lens with a physical structure that supports the second optical member and the anchoring system.

The intraocular lens according to the present invention may comprise a retaining system selected from temporary blocking systems which block the deformation and diameter of the lens during implantation of the lens during the surgical act, temporary blocking which block the deformation of the lens during a particular period after implantation of the intraocular lens to stabilize the anchorage between the intraocular lens and the capsular bag of the crystalline lens, and combinations of said temporary blocking systems. Thus, for example, implantation of the intraocular lens may be combined with a tension ring to stretch the lens and thereby block its accommodative internal tension during the surgical act, thereby facilitating the anchoring process to the capsular bag of the crystalline lens. The tension ring may be dismountable during the last steps of the surgical act, or may be biodegradable and absorbable at a time after implantation. This latter option favors the actuation of bio-adherence mechanisms during a certain period of operation.

The second optical member and the first optical member are coupled to each other by a mechanical connecting system. In this case, the first optical member and the second optical member may be individual elements which are separated from each other before their injection into the eye, in which case the mechanical connecting system is designed to allow coupling the second optical member to the first optical member after the first optical member has been injected into the eye, and vice versa.

The mechanical connecting system may be designed to allow separation of the second optical member from the first optical member after the intraocular lens has been implanted by a surgical act, and to allow coupling of a new second optical member after the second optical member has been separated and extracted. Alternatively, the second optical member may be undetachably joined to the first optical member.

In an embodiment of the invention, the mechanical connecting system comprises a plurality of flanges emerging from the first optical element adjacently to a first of the curved sides of the second optical member, and holding portions of a peripheral area of the second of the curved sides of the second optical member which is opposed to the first curved side. The flexible flanges comprise respective bent free end portions which contact the second curved side of the second optical member and press the first curved side of the second optical member against the first surface of the first optical member. At the same time, the bent, free end portions slide on said first curved side when the first optical element deforms in response to the traction forces received.

Regarding surgical implantation and differing from other prior approaches described in prior art, for the surgical implantation and the correct performance of the intraocular lens with capacity of accommodation which is the object of this invention, integrity of the capsule of the crystalline lens is not necessary. In fact, according to the invention the capsule of the crystalline lens only acts as an element that transmits forces in the equatorial region.

This entails very important advantages compared to other ways of restoring accommodation. First, as the integrity of the anterior capsule is no necessary, the intraocular lens which is the object of the invention may be implanted by means of capsulorrhexis, the same as conventional intraocular lenses. Second, integrity of the posterior capsule is not necessary either, which makes posterior capsulotomy tolerable to remove capsular opacifications which generally generate after surgery. On the other hand, as it also has been mentioned, capsular fibrosis (mainly equatorial) may be considered an advantageous process for the anchoring system that may reinforce and even constitute the fastening mechanism.

The use of a laser during the surgical act may also be considered to cut the capsule with a very precise control of the shape of the rhexis. The resulting rhexis may have a circular shape as conventional capsulorrhexis although with an accurate diameter, or it may adopt more sophisticated shapes that allow flanges or bendings that facilitate anchoring systems by clamping or adherence, under a greater control of the tensions applied to the lens.

In other embodiments of the lens, the lens implantation process and particularly fastening the capsule is guided by means of endoscopy to facilitate positioning thereof in the area of interest.

BRIEF DESCRIPTION OF THE DRAWINGS

Hereafter, aspects and embodiments of the invention will be described with an illustrative and non-limiting nature on the grounds of schematic drawings, wherein

FIG. 7A is a lateral sectional view of the intraocular lens according to a sixth embodiment, with the first optical member in an accommodated condition;

FIG. 7B shows an optical simulation of the performance of the intraocular lens according to a sixth embodiment, with the first optical member in an accommodated condition;

FIG. 7C is a lateral sectional view of the intraocular lens according to the sixth embodiment, with the first optical member in a disaccommodated condition;

FIG. 7D shows an optical simulation of the performance of the intraocular lens according to the sixth embodiment, with the first optical member in a disaccommodated condition;

FIG. 8A is a lateral sectional view of the intraocular lens according to a seventh embodiment, with the first optical member in an accommodated condition;

FIG. 8B is a lateral sectional view of the intraocular lens according to the seventh embodiment, with the first optical member in a disaccommodated condition;

FIG. 8C is a top plan view of the intraocular lens according to the seventh embodiment;

FIG. 8D is a top perspective view of the intraocular lens according to the seventh embodiment.

Figure 1A:
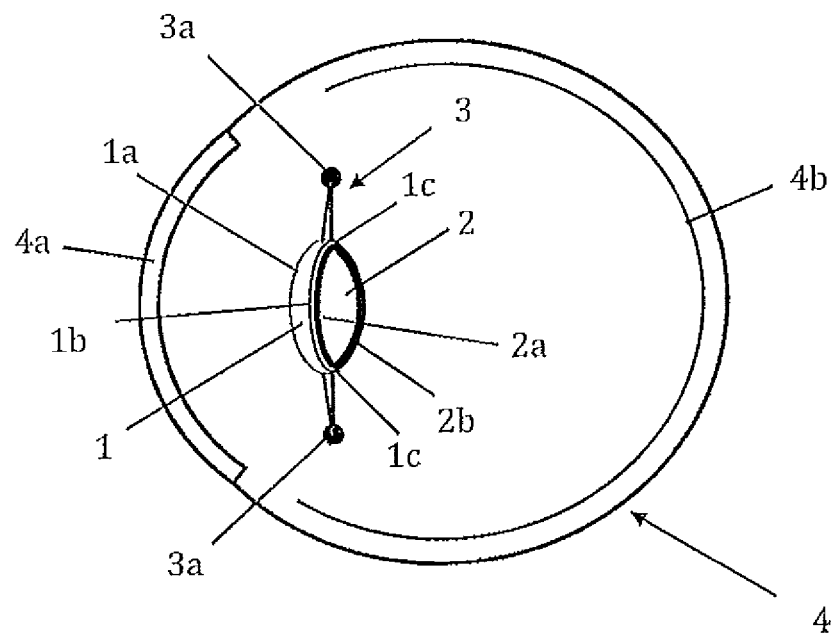
FIG. 1A is a schematic lateral sectional view of a first embodiment of the intraocular lens of the invention implanted in an eye with its first optical member in a condition of accommodation.

In these figures, there appear reference signs which identify the following elements:
 1 first optical member
 1a, 1a' anterior surface
 1b, 1b' posterior surface
 1c equatorial region
 1d inner surface
 1e outer radial extensions
 1f throughholes
 2 second optical member
 2a anterior curved surface
 2b posterior curved surface
 2c halves
 2d convex portion
 2e concave portion
 3 anchoring system
 3a, 3a' anchoring points
 3b haptics
 3c flexible flanges
 3d bent end portions
 3e anchor ring
 3f inner projection
 3g bore
 3h locking pin
 3i head
 3j slot
 4 eyeball
 4a cornea
 4b retina

MODES TO CARRY OUT THE INVENTION

In all embodiments shown in the figures, the intraocular lens with accommodation capacity comprises an optical power system with a first optical member -1- having a dynamic optical power and a second optical member -2- having a fixed optical power, as well as an anchoring system -3- to anchor the first optical member -1- to at least a portion of the capsular bag (not shown in the figures) of the eyeball -4-. The optical members shown in the figures are not to real scale and some features of the lens (such as the curvatures of the surfaces thereof) have been exaggerated for a correct visualization and illustration of behavior of the invention.

The first optical member -1- comprises two surfaces -1a, 1b- respectively corresponding to an anterior surface -1a- and a posterior surface -1b-, at least one of which has a curvature that is capable of becoming deformed elastically in response to traction forces of the ciliary muscle of the eye, an equatorial region -1c- about the surfaces -1a, 1b-, and at least a preformed deformable material with a variable optical power. The second optical member -2- is joined to the first optical member -1- in such a manner that at least respective central portions of one of the curved sides -2a, 2b- of the second optical member -2- and of at least one of the surfaces -1a, 1b- of the first optical member -1- are in contact with each other.

The second optical member -2- has a fixed optical power and comprises an anterior curved surface -2a- and a posterior curved surface -2b-. The second optical member -2- is associated to the first optical member -1- in such a manner, that the first optical member -1- and the second optical member -2- jointly have a joint optical power determined by the fixed optical power of the second optical member -2- and the dynamic optical power of the first optical member -1-. The joint optical power is variable between a condition of disaccommodation where the intraocular is variable between a condition of minimum optical power corresponding to a condition of disaccommodation where the intraocular lens is capable of focusing the eye to a far vision distance, and a condition of accommodation where the intraocular lens is capable of focusing the eye to a reading distance.

The anchoring system -3- anchors the first optical member -1- to at least a portion of the capsular bag of the crystalline lens (not shown in the figures) and is designed to transmit to the first optical member -1-, traction forces generated by the ciliary muscle and transmitted to the capsular bag through zonular fibers. As known, in its natural condition the capsular bag comprises an anterior capsule, a posterior capsule and an equatorial capsule. The anchoring system -3- may be selected, for example, from mechanical fastening mechanisms, biocompatible adhesive systems and processes, microstructure systems fostering capsular fibrosis, and combinations thereof.

The first optical member -1- and the anchoring system -3- are designed to change the curvature of at least one of the surfaces -1a, 1b- of the first optical member -1 progressively between a maximum curvature corresponding to the condition of maximum accommodation in response to a minimum effective traction force of the ciliary muscle received by the anchoring system -3-, and a minimum curvature corresponding to the condition of disaccommodation in response to a maximum effective traction force of the ciliary muscle received by the anchoring system -3-.

Figure 1B:
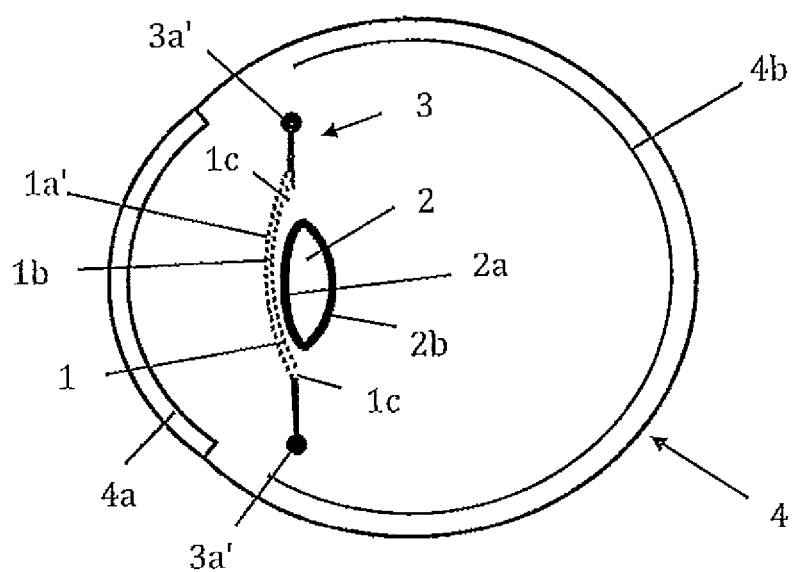
FIG. 1B is a schematic view corresponding to the first embodiment of intraocular lens according to FIG. 1A with the first optical element in a condition of disaccommodation.
Figure 2:
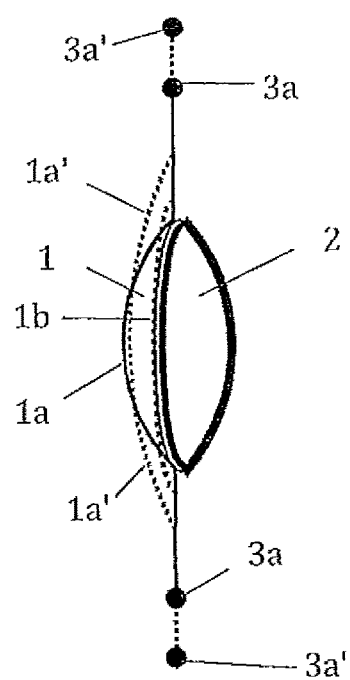
FIG. 2 is another schematic view corresponding to the first embodiment of intraocular lens according to FIGS. 1A and 1B.

In the embodiment illustrated in FIGS. 1A, 1B and 2, an embodiment is shown where the first optical member -1- is positioned in an anterior position i.e. closer to the cornea -4a- and in front of the second optical member -2- which is positioned in a posterior position i.e. closer to the retina -4b-

The anterior side -2a- of the second optical member -2- is in contact with the posterior surface -1b- of the first optical member -1-. In the accommodated condition shown by continuous lines in FIGS. 1A and 2, the anterior surface -1- of the first optical member -1- has a maximum curvature corresponding to a condition of maximum joint optical power of the joint optical powers of the first optical member -1- and the second optical member -2-, corresponding to a reading distance, whilst the dotted lines appearing in FIGS. 1A and 2 show the condition of disaccommodation where the anterior surface -1a- of the first optical member -1- has a minimum curvature corresponding to a minimum joint optical power corresponding to a far vision distance. On its part, the posterior surface -1b- of the first optical member -1- is always in contact with the anterior curved side -2a- of the second optical member -2-, so that the curvature of the posterior side -1b- of the first optical member always maintains the same curvature as determined by the curvature of the anterior curved side -2a- of the second optical member -2-.

The equatorial region -1c- of the first optical member -1- is joined to an anchoring system 3 with anchoring points -3a, 3a'- that are anchored to the capsular bag of the crystalline lens (not shown in the drawings). When the ciliary muscle (not shown in the drawings) is contracted, the anchoring points are at a distance close to the first optical member -1- which the adopts the maximum curvature of its anterior surface -1a- which can be seen in FIG. 1A. When the ciliary muscle relaxes, the anchoring points -3a- progressively move away from each other until reaching their farthest positions -3a'- shown in FIGS. 1B and 2, due to the traction force exerted by the ciliary muscle onto the capsular bag of the crystalline lens where the anchoring points -3a, 3a'- of the anchoring system -3- are anchored. The anchoring system -3- thus transmits these traction forces to the first optical member -1- until the anterior surface -1a- thereof adopts the admitted minimum curvature identified by reference -1a'- in FIGS. 1B and 2.

Figure 3:
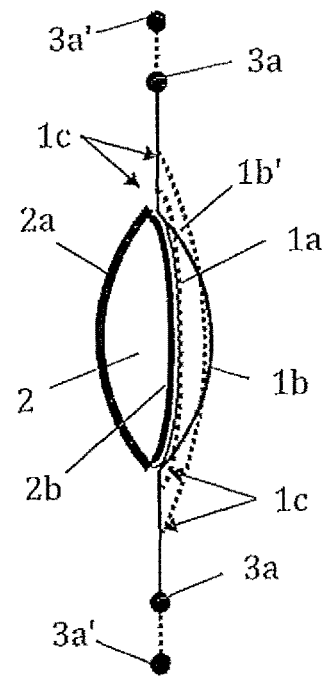
FIG. 3 is a schematic lateral sectional view of the intraocular view according to a second embodiment.

FIG. 3 shows a second embodiment of the intraocular lens according to the present invention, where the first optical member -1- is positioned behind the second optical member -2-, such that the posterior side -2b- of the second optical member -2- is in contact with the anterior surface -1a- of the first optical member -1-, so that the second optical member -2- is closer to the cornea whilst the first optical member -1- is farther away from the cornea.

In the accommodated condition shown by continuous lines in FIG. 3, the posterior surface -1b- of the first optical member -1- has a maximum curvature corresponding to a joint condition of maximum refraction of the refraction indices of the optical members -1, 2-, corresponding to a reading distance, whilst the dotted lines show the condition of disaccommodation where the posterior surface -1b- of the first optical member -1- has a minimum curvature corresponding to a joint condition of minimum refraction, which corresponds to a far vision distance. On its part, the anterior surface -1a- of the first optical member -1- is always in contact with the curved posterior side of the second optical member -2-, so that the curvature of the anterior surface -1a- of the first optical member -1- always maintains the same curvature determined by the curvature of the posterior curved side -2a- of the second optical element -2-.

The same as in the first embodiment described above, the equatorial region -1c- of the first optical member -1- is joined to the anchoring system -3- which has anchoring points -3a, 3a'- that are anchored to the capsular bag of the crystalline lens (not shown in the figures). When the ciliary muscle (not shown in the figures) is contracted, the anchoring points are located at a distance close to the first optical member -1- that then adopts the shape and maximum curvature of its posterior surface -1b- that can be seen by the continuous lines in FIG. 3. When the ciliary muscle relaxes, the anchoring points -3a- move away from each other progressively until reaching their farthest positions -3a'- shown by dotted lines in FIG. 3, due to the traction force exerted by the ciliary muscle onto the capsular bag of the crystalline lens where the anchoring points -3a, 3a'- of the anchoring system -3- are anchored. The anchoring system -3- thus transmits these traction forces to the first optical member -1- until the posterior surface -1b- thereof adopts the admitted minimum curvature identified by reference -1b'- in FIG. 3.

Figure 4:
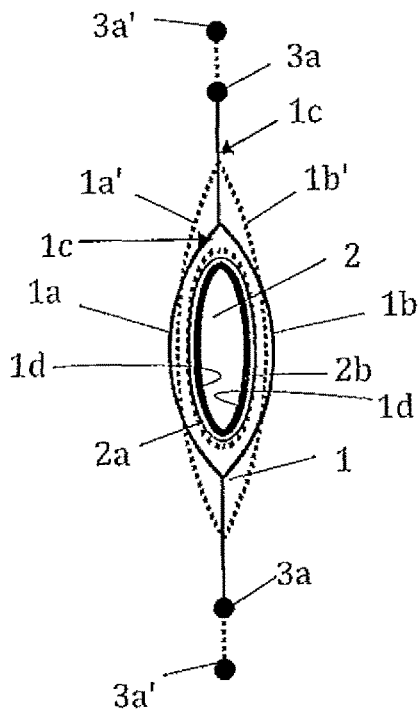
FIG. 4 is a schematic lateral sectional view of the intraocular view according to a third embodiment.

In the third embodiment of the intraocular lens according to the invention as illustrated o FIG. 4, the first optical member -1- externally surrounds the curved sides -2a, 2b- of the second optical member -2-, and the two curved sides -2a, 2b- of the second optical member -2- are arranged adjacent to respective inner surfaces -1d- of the first optical member -1-, so that the curved sides -2a, 2b- of the second optical member -2- are in contact with the inner surfaces -1d- of the first optical member -1-.

In the accommodated condition shown by continuous lines in FIG. 4, the anterior and posterior surfaces -1a, 1b- of the first optical member -1- have maximum curvatures corresponding to a condition of maximum joint optical power of the joint optical powers of the optical members -1, 2-, which corresponds to a reading distance, whilst the dotted lines show the condition of disaccommodation where said surfaces -1a, 1b- of the first optical member -1- have minimum curvatures corresponding to a condition of minimum joint optical power of the joint optical powers of the optical members -1, 2-, which corresponds to a far vision distance. On their part, the inner surfaces -1d- of the first optical member -1- are always in contact with the curved sides -2a, 2b- of the second optical member -2-. Thereby, the curvatures of the inner surfaces -1d- always maintain the same curvatures determined by the curvatures of the curved surfaces -2a, 2b- of the second optical member -2-.

The same as in the above described embodiments, the equatorial region -1c- of the first optical member -1 is joined to the anchoring system -3- by anchoring points -3a, 3a'- which are anchored to the capsular bag of the crystalline lens (not shown in the figures). When the ciliary muscle is contracted, the anchoring points are located at a distance close to the first optical member -1- that then adopts the shape and maximum curvature of its anterior and posterior surfaces -1a, 1b- that can be seen by the continuous lines in FIG. 4 determined by the preform of the first optical member -1-.

When the ciliary muscle relaxes, the anchoring points -3a- move away from each other progressively until reaching their farthest positions -3a'- shown by dotted lines in FIG. 4, due to the traction force exerted by the ciliary muscle onto the capsular bag of the crystalline lens where the anchoring points -3a, 3a'- of the anchoring system -3- are anchored. The anchoring system -3- thus transmits these traction forces to the first optical member -1- until the posterior surface -1b- thereof adopts the admitted minimum curvature identified by reference -1b'- in FIG. 4.

Figure 5:
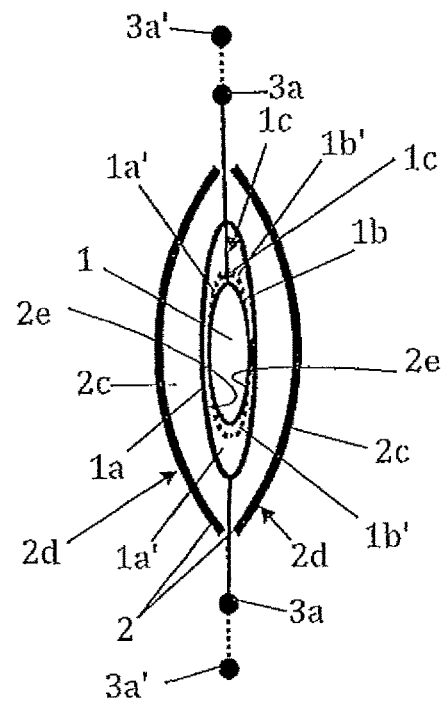
FIG. 5 is a schematic lateral sectional view of the intraocular view according to a fourth embodiment.

In the fourth embodiment of the intraocular lens according to the present invention as illustrated in FIG. 5, the first optical member -1- is located between respective halves -2c- of the second optical member -2-, which comprise respective outer convex portions -2d- and respective inner concave portions -2e-. The convex portion -2d- of one of said halves -2c- comprises said anterior curved side -2a- and the convex portion -2d- of the other of said halves -2c- comprises said posterior curved side -2b-. The surfaces -1a, 1b- of the first optical member -1- are arranged adjacent to the inner concave portions -2e- of the second optical member -2-, so that the surfaces -1a, 1b- of the first optical member -1- are in contact with the concave portions -2e- of the halves -2c- of the second optical member -2-.

In the accommodated condition shown by continuous lines in FIG. 5, the anterior and posterior surfaces -1a, 1b- of the first optical member -1- have maximum curvatures corresponding to a condition of maximum joint optical power of the joint refraction indices of the optical members -1, 2-, which corresponds to a reading distance, whilst the dotted lines show the condition of disaccommodation where said surfaces -1a, 1b- of the first optical member -1- have minimum curvatures corresponding to a condition of minimum joint optical power which corresponds to a far vision distance. On their part, at least the central portions of the anterior -1a, 1a'- and the posterior -1b, 1b'- surface are always in contact with the central portions of the concave portion -2e- of the second optical member -2-, so that the curvatures of the central portions of the anterior and posterior surfaces -1a, 1b- of the first optical member -1- always maintain the same curvatures determined by the central portions of the curvatures of the concave portions 2e- of the second optical member -2-.

Analogous to the above described embodiments, the equatorial region -1c- of the first optical member -1- is joined to the anchoring system -3- by anchoring points -3a, 3a'- which are anchored to the capsular bag of the crystalline lens (not shown in the drawings). When the ciliary muscle is contracted, the anchoring points are at a distance close to the first optical member -1-, which then adopts the shape and maximum curvature of its anterior and posterior surfaces -1a, 1b- which can be seen by continuous lines in FIG. 5. When the ciliary muscle relaxes, the anchoring points -3a- move away from each other progressively until reaching their farthest positions shown in FIG. 5 by dotted lines, so that a traction force is produced by the ciliary muscle, acting on the capsular bag of the crystalline lens to which the anchoring points -3a, 3a'- of the anchoring system -3- are anchored. The anchoring system -3- thus transmits these traction forces to the first optical member -1- until its anterior and posterior surfaces -1a, 1b- adopt the admitted minimum curvatures as identified in FIG. 5 by references -1a', 1b'-.

In the fifth embodiment of the ophthalmic lens shown in FIGS. 6A-6D, the first optical member -1- is, the same as in the embodiment of FIG. 3, located behind the second optical member -2-. The anchoring system -3- comprises a mechanical fastening system which is anchored in the tissue of the capsular bag.

The mechanical fastening system comprises a plurality of retaining parts in the form of haptics -3b- that are arranged radially and jointly connected to the first optical member -1- at its equatorial region -1c- and which have free ends in the shape of transverse plates that constitute discrete sets of anchoring points -3a- which are uniformly distributed along the equatorial region of the first optical member in the tissue of the capsular bag of the crystalline lens. Biocompatible systems or processes may be used in order to contribute to the strength of the anchorage between the plates of the haptics and the tissue of the capsular bag. As it can be seen, the intraocular lens of FIGS. 6A-6D has a tridimensional structure with a shape designed to emulate the shape of the equatorial capsule of the capsular bag of the crystalline lens, and to thereby maintain the anterior capsule separated from the posterior capsule, and to maintain the traction forces of the zonular fibers distributed substantially in the same way as in the natural eye.

The second optical member -2- is coupled to the first optical member -1- by means of a mechanical coupling system comprising a plurality of flexible flanges -3c- emerging from the first optical member adjacent to a first of the curved sides of the second optical member -2-, specifically its posterior curved side -2b-, and they hold portions of a peripheral region of a second one of said curved sides i.e. the anterior curved side -2a- of the second optical member -2- that is opposite to the posterior curved side -2b-. The flexible flanges -3c- comprise respective bent end portions that contact the anterior curved surface -2a- of the second optical member -2- and press the posterior curved side -2b- of the second optical member -2- against the anterior surface -1a- of the first optical member -1-, so that the bent free end portions -3d- slide on the anterior curved side -2a- when the first optical member -1- deforms in response to the traction forces received.

Figure 6A:
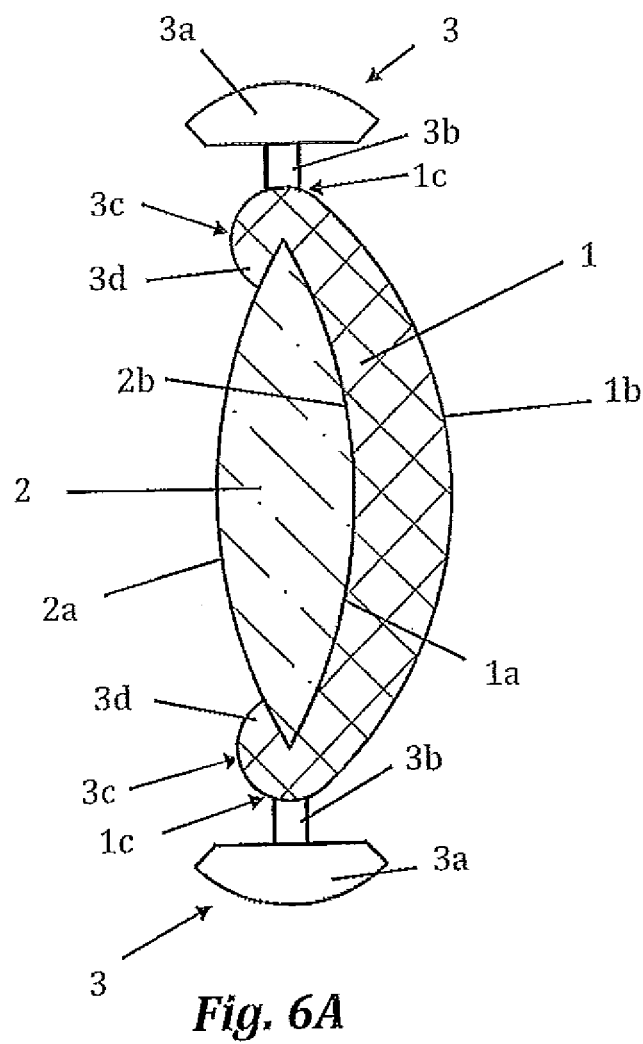
FIG. 6A is a lateral sectional view of the intraocular lens according to a fifth embodiment, with the first optical member in an accommodated condition.
Figure 6B:
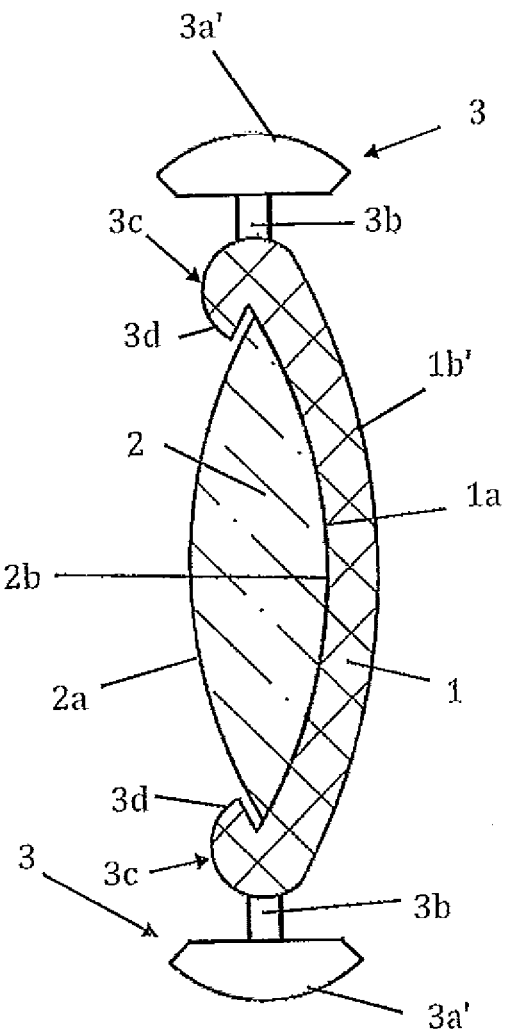
FIG. 6B is a lateral sectional view of the intraocular lens according to the fifth embodiment, with the first optical member in a disaccommodated condition.
Figure 6C:
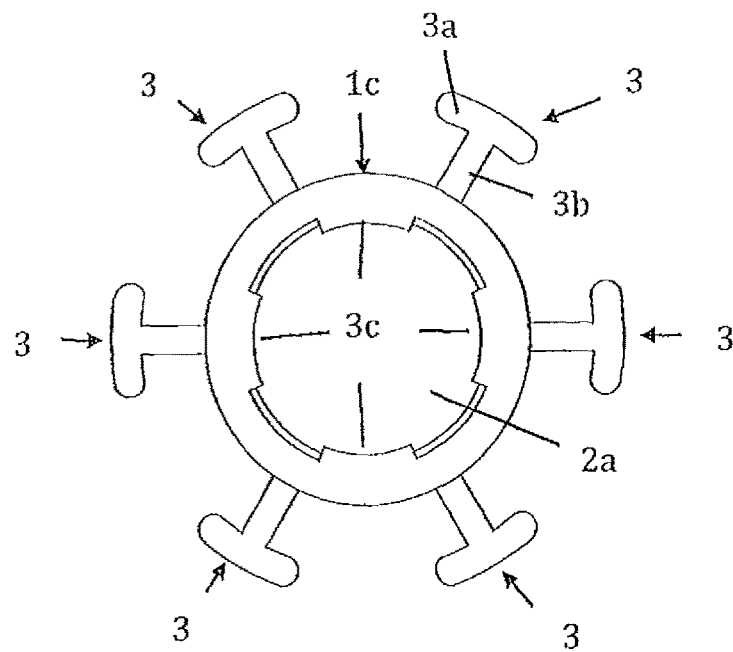
FIG. 6C is a top plan view of the intraocular lens according to the fifth embodiment.
Figure 6D:
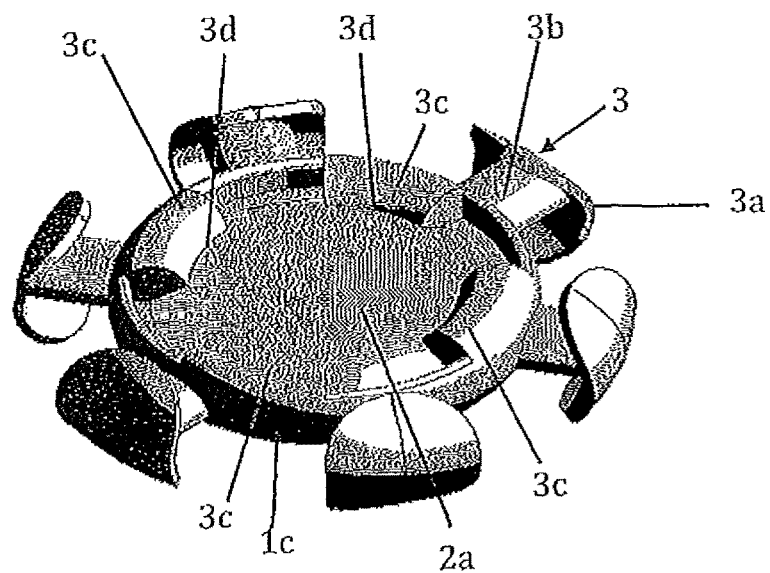
FIG. 6D is atop perspective view of the intraocular lens according to the fifth embodiment.

In the accommodated condition shown in FIG. 6A, the posterior surface -1b- of the first optical member -1- has a maximum curvature corresponding to a condition of maximum joint optical power of the joint optical powers of the optical members -1, 2- corresponding to a reading distance, whilst in the condition of disaccommodation illustrated in FIG. 6B the posterior surface -1b- of the first optical member -1- has a minimum curvature corresponding to a minimum joint optical power corresponding to a far vision distance. On its part, the anterior surface -1a- of the first optical member -1- is always in contact with the curved posterior side -2b- of the second optical member -2-, so that the curvature of the anterior surface -1a- of the first optical member -1- always maintains the same curvature determined by the curvature of the posterior side -2b- of the second optical member -2-.

The same as in the above described first embodiment, the equatorial region -1c- of the first optical member -1- is joined to an anchoring system -3- consisting of haptics -3b- the respective plates of which constitute the anchoring points -3a, 3a'- which are anchored in the capsular bag of the crystalline lens. When the ciliary muscle is contracted, the anchoring points are at a distance close to the first optical member -1- which then adopts the shape and maximum curvature of its posterior surface which may be seen in FIG. 6A. When the ciliary muscle relaxes, the anchoring points -3a- move away from each other progressively until reaching their farthest positions -3a'- shown in FIG. 6B, so that a traction force is produced by the ciliary muscle acting on the capsular bag of the crystalline lens to which the haptics -3b- of the anchoring system -3- are anchored. The anchoring system -3- thus transmits these traction forces to the first optical member -1- until the posterior surface thereof adopts the admitted minimum curvature identified by reference -1b'- in FIG. 6B.

In the fifth embodiment of the invention shown in FIGS. 6A-6D, the first optical member -1- provides the dimensional stability required by the lens, and serves at the same time as a support for the second optical member -2-. The lenticular second optical member -2- stays positioned or housed in front of the first optical member -1- fastened only by the flexible flanges -3c-. Although there is no set fixation between both optical members, the flexible flanges -3c- cause that there is neither a free movement of the second optical member -2- in respect of the first optical member -1-. Thus, movement of the anterior surface -1a- of the first optical member -1- is limited by the shape of the posterior curved side -2b- of the second optical member -2-. The anterior surface -1a- of the first optical member -1- and the posterior curved side -2b- of the second optical member -2- tend to form an interface surface which is much more stable than the posterior surface -1b- of the first optical member -1- that is capable of a more free deformation and, in particular, of significant curvature changes. These curvature changes may entail changes in thickness.

In this embodiment, the second optical member -2- is similar to a common monofocal intraocular lens but without haptics, and it is flexible and foldable. The flexible flanges -3b- that retain the second optical member -2- are designed, together with the first optical element -1-, in such a manner that the second optical member can be inserted and released. This possibility makes it possible that both members may be separately implanted in the eye, which potentially may reduce the size of the incision which is necessary for the implantation. This capacity also makes the second optical member -2- exchangeable in a surgical act so as to change the joint optical power of the intraocular lens, adjusting it to the patient's demand. The anterior position of the second optical member -2- favors that the second optical element is exchangeable.

To facilitate handling of the assembling of both optical members or of releasing the second optical member -2-, the equator of the second optical member -2- is accessible to the surgeon through the spaces between the flexible flanges -3c- by means of a specific surgical tool that may be used as a lever.

In FIGS. 6A-6D it may further be observed that the haptics -3b- which constitute the anchoring system according to this embodiment are fixedly linked to the first optical member at its equatorial region -1c-.

The sixth embodiment of the intraocular lens according to the present invention as illustrated in FIGS. 7A-7D differs from the above described fifth embodiment with reference to FIGS. 6A-6D in that the curved sides -2a, 2b- of the second optical member -2- are flatter than in said fifth embodiment.

In this sixth embodiment, the first optical member -1- consists of a single material, particularly polyhydroxiethyl-metacrilate (pHema) copolymerized with further substance to increase hydrophily and flexibility thereof maintaining its biocompatibility. On the other hand, the second optical member is constituted of a different material. In this example of embodiment of the invention, the mechanical properties of the material are not as critical as its optical properties. It is recommendable using a material with a high refraction index, which favors making high power lenses with relatively small thicknesses. Specifically, in this example PMMA described by means of a refraction index of 1.49, a Young's Modulus of 1100 MPa and a Poisson Coefficient of 0.42, have been chosen.

Further the anchoring system -3- and its haptics -3b- which are provided with transverse plates is preferably constituted of rigid materials to favor transmission of forces with minimal losses, and therefore PMMA has again been used. In this embodiment a mixed technique has been chosen for capsular fixing to the capsular of the crystalline lens which is based on the combined use of bioadhesives and in promoting bioadherence. The surfaces of the intraocular lens which will be in contact with the capsule, specifically the transversal plates of the haptics -3b- have a highly porous finishing that facilitates the application of bioadhesive and bioadherence of the capsular tissue. Furthermore, they incorporate a biocompatible coating for promoting bioadherence. As an alternative to the use of bioadhesives, bonding to the capsule may be favored even more by means of a filamentous velcro-type structure.

In any case, to facilitate the surgical implantation act of the intraocular lens, this latter may have a biodegradable and absorbable coating such as silk or collagen, which retains the bioadhesive or conceals and neutralizes the structure promoting bioadherences. When disappearing a short time after implantation, local application of the bioadhesive or of the process of bioadherence is triggered.

In order to illustrate the performance of the intraocular lens according to the sixth embodiment, first a mechanical simulation in a finite element model has been carried out. For this simulation of the mechanical properties of the intraocular lens shown in its accommodated condition in FIG. 7A and it its disaccommodated condition in FIG. 7C, a Mooney-Rivlin Model of hyperelastic material with three parameters; C01=0.142 MPa, C10=1500 Pa, C11=21.4 MPa with a Young's Modulus equivalent to 7 MPa, was used. The refraction index of this material used for the optical simulation is about 1.52, which may be modulated depending on the copolymers used, at a temperature of 350° C.

Application of a net force along the 6 haptics, of 0.09 N, 0.015 at each haptic, consistent with the force applied by the ciliary muscle to the capsular bag, causes a diametrical expansion of 0.05 mm of the intraocular lens at the level of the haptics -3b-, the same as that for the first optical member -1-, as the haptics -3b- are considered to be rigid. This diametrical expansion is sufficient to cause a substantial change in the curvature of the posterior surface -1b- of the first optical member -1- which, according to the computer simulation, passes from 5 mm in the absence of traction forces, to 5.52 mm at the total net force. Except for the central thickness of the first optical member -1- changing slightly from 1.12 mm to 1.145 mm, the remaining geometrical parameters of the intraocular lens remain unaltered.

An optical simulation by means of a ray tracing program through the optical surfaces according to the previously calculated geometry for this example embodiment of the invention and in combination with a model of the eye, determine an optical power of 24.75 D in the position of accommodation (FIG. 7B) in the absence of external forces, and of 22 D under the traction of forces in the position of disaccommodation (FIG. 7D). Unlike other approaches, the dioptric change, 2.75 diopters in this embodiment of the invention, occurs in the same direction as in natural accommodation, providing the eye with more power -near vision- when the ciliary muscle is contracted due to an accommodative effort.

Thanks to the geometry of the intraocular lens and to the properties of the pHema material, the intraocular lens allows folding the anchoring system -2- and the first optical member -1-, and it can be implanted through an incision of 5 mm in two steps. In a first step, the first optical member -1- and the anchoring system -3- which is based on the haptics -3b- that are fixed to the capsule of the crystalline lens by means of a bioadhesive at short term and by bioadherence process at long term, are implanted. In a second step the second optical member -2- is implanted.

In the seventh embodiment of the invention shown in FIGS. 8A-8D, the first optical member -1- is located in an anterior position and the second optical member -2- is positioned in a posterior position. The posterior surface -1b- of the first optical member -1- is bonded to the anterior curved side -2a- of the second optical member -2-. Thereby, the bonding surface acts as a retaining element for the deformation of the posterior surface -1b- of the first optical member -1- and facilitates the curvature change of the anterior surface -1a- of the first optical member -1-. In this embodiment, the second optical member is not exchangeable, and thus the far vision power is not adjustable once the intraocular lens has been implanted.

In the accommodated condition shown in FIG. 8A, the anterior surface of the first optical member -1- has a maximum curvature corresponding to a condition of maximum joint refraction of the joint refraction indices of the optical members -1, 2- that corresponds to reading distance, whilst FIG. 8B illustrates the condition of disaccommodation where the anterior surface -1a- of the first optical member -1- has a minimum curvature corresponding to a condition of minimum joint refraction that corresponds to a far vision distance. On its part, the posterior surface -1b- of the first optical member -1- is fixedly joined to, and thus always in contact with the anterior curved side -2a- of the second optical member -2- so that the curvature of the posterior surface -1b- of the first optical member -1- always maintains the same curvature determined by the curvature of the anterior curved side -2a- of the second optical member -2-.

In FIGS. 8A-8D the first optical member -1- joined to the anchoring system -3- by means of a fixing system, is shown. The fixing system comprises a plurality of outer radial extensions -1e- that emerge from the equatorial region -1c- of the first optical member -1-, and an anchor ring -3e- with a plurality of inner projections -3f- which protrude from the inner periphery of the anchor ring -3e-. In this embodiment, the anchoring points -3a, 3a'- are circular segments in the anchor ring -3e- at the level of each of the inner projections -3f-. The material of the anchor ring -3e- is rigid in the angular regions corresponding to the a anchoring points -3a, 3a'- to facilitate transmission of forces, but soft and elastic between two consecutive anchoring points to facilitate the expansion or compression of the anchor ring during operation of the lens.

The free ends of the inner projections -3f- comprise slots into which there fit free end portion of the radial extensions. Each of the radial extension -1e- is provided with a through-hole aligned with bores -3g- penetrating through lateral walls of the slot -3j-, in such a manner that each interior projection -3f- may be immobilized in the slot -3j- by a locking pin -3h- which extends through the bore -3g- and the respective throughhole -1f- and comprises respective thickened heads -3i- at its ends so that the locking pin -3h- is firmly retained.

This fixing system allows assembling the first optical member -1- and the anchoring system -3- before surgery, and in this case the these elements are inserted jointly into the eye. Alternatively, they may be inserted during surgery, the anchoring system being implanted prior to assembling the first optical member -1- and the second optical member -2-.

In the embodiment shown in FIGS. 8A-8D, the equatorial region -1c- of the first optical member -1- is joined through the fixing system to the anchor ring -3e- which comprises the anchoring points -3a, 3a'- anchored to the capsular bag of the crystalline lens (not shown in the figures). When the ciliary muscle (not shown in the figures) contracts is contracted, the anchoring points -3a- are at a closer distance to the first optical member -1- which then adopts the shape and maximum curvature of its anterior surface -1a- that can be seen in FIG. 8A. When the ciliary muscle relaxes, the anchoring points move away from each other progressively until reaching their farthest positions -3a'- shown in FIG. 8B, due to the traction force exerted by the ciliary muscle when relaxing, onto the capsular bag of the crystalline lens where the anchoring points -3a, 3a'- of the anchoring system are anchored. Through the above described fixing system the anchoring system transmits these traction forces to the first optical member -1- until the anterior surface -1a- thereof adopts the minimum curvature identified by reference 1a'- in FIG. 8B.

In optical and mechanical simulations of the intraocular lens according to the seventh embodiment, the same materials and forces as in the preceding example are used. And in the same way as in the case of the sixth embodiment, the optical and mechanical simulations show a change in power of 2.75 diopters as a response to the traction forces existing in the eye, due to a change in curvature of the anterior surface of the first optical member -1-.

The invention claimed is:

1. Intraocular lens with accommodation capacity comprising:
   an optical power system comprising a first optical member (1) with variable and dynamic optical power and which comprises two surfaces (1a, 1b) respectively corresponding to an anterior surface (1a) and a posterior surface (1b) at least one of which having a curvature that is capable of becoming deformed elastically in response to traction forces of the ciliary muscle of the eye, an equatorial region (1e) about said surfaces (1a, 1b), as well as a second optical member (2) with a fixed optical power, with a curved anterior side (2a) and a curved posterior side (2b), the second optical member (2) being associated to the first optical member (1) in such a manner that the first optical member (1) and the second member (2) have a joint optical power determined by a combination of the fixed optical power of the second optical member (2) and the dynamic optical power of the first optical member (1),
   an anchoring system (3) to anchor the first optical member (1) to at least a portion of the capsular bag of the crystalline lens, to transmit to the first optical member (1) traction forces generated by the ciliary muscle and transmitted to the capsular bag by zonular fibers, the capsular bag comprising, in its natural state, an anterior capsule, a posterior capsule and an equatorial capsule, the anchoring system (3) selected among mechanical fastening systems, biocompatible adhesive systems, microstructure systems fostering capsular fibrosis, and combinations thereof,
   wherein the second optical member (2) is joined to the first optical member (1) such that at least respective central portions of one of the curved sides (2a, 2b) of the second optical member (1) and of at least one of the surfaces (1a, 1b) of the first optical member (1) are in contact with each other;
   the joint optical power is variable between a condition of minimum optical power corresponding to a condition of disaccommodation where the intraocular lens is capable of focusing the eye to a far vision distance, and a condition of accommodation where the intraocular lens is capable of focusing the eye to a reading distance;
   wherein the first optical member is made of a preformed deformable material and has a predetermined preform of maximum curvature and maximum optical power in its accommodation position;
   the first optical member (1) and the anchoring system (3) designed to change the curvature of at least one of the surfaces (1a, 1b) of the first optical member (1) progressively between the predetermined preform maximum curvature corresponding to the condition of maximum accommodation in response to a minimum effective traction force of the ciliary muscle received by the anchoring system (3), and a minimum curvature corresponding to the condition of disaccommodation in response to a maximum effective traction force of the ciliary muscle received by the anchoring system (3); and
   wherein the anchoring system is a discrete set of more than three anchoring points to anchor the first optical member (1) to at least a portion of the capsular bag of the crystalline lens.

2. Intraocular lens, according to claim 1, characterized in the first optical member (1) is placed in a position selected among:
   an anterior position where it is placed in front of the second optical member (2), and at least a central portion of the anterior side (2a) of the second optical member (2) is in contact with at least a central portion of the posterior surface (1b) of the first optical member (1); and
   a posterior position where it is placed behind the second optical member (2), and at least a central portion of the posterior side (2b) of the second optical member (2) is in contact with at least a central portion of the anterior surface (1a) of the first optical member (1).

3. Intraocular lens, according to claim 1 or 2, characterized in that the anchoring system comprises retaining parts (3b) to capture and retain tissue of the capsular bag of the crystalline lens.

4. Intraocular lens, according to claim 1, characterized in that it comprises a microstructure system fostering capsular fibrosis comprising a biocompatible material with microstructures that foster capsular fibrosis.

5. Intraocular lens, according to claim 1, characterized in that the anchoring system (3) is designed to become fastened to at least a portion of a side of the capsular bag of the crystalline lens.

6. Intraocular lens, according to claim 1, characterized in that it comprises a tridimensional structure having a shape which emulates the shape of the equatorial capsule of the capsular bag of the crystalline lens of the eye, and which maintains the anterior capsule spaced from the posterior capsule and the traction forces of the zonular fibers substantially equal than in the natural eye.

7. Intraocular lens, according to claim 1, characterized in that the anchoring system is selected from anchoring systems comprising discrete anchoring points (3a, 3a') which are uniformly distributed along the equatorial region (1e) of the first optical member (1) and continuous anchoring systems which extend along said equatorial region (1c).

8. Intraocular lens, according to claim 1, characterized in that the first optical member (1) comprises a plurality of layers of different preformed deformable materials.

9. Intraocular lens, according to claim 1, characterized in that the first optical member (1) comprises at least one layer of preformed deformable material combined with a moldable filler material.

10. Intraocular lens, according to claim 1, characterized in that it comprises a retaining system selected from temporary blocking systems which block the deformation and diameter of the intraocular lens while the intraocular lens is being implanted in a surgical operation, temporary blocking systems which block the deformation and diameter of the intraocular lens during a predetermined period after the intraocular lens has been implanted to stabilize anchorage between the intraocular lens and the capsular bag, and combinations of said blocking systems.

11. Intraocular lens, according to claim 1, characterized in that it has a limiting system imposing a physical limit to reduction of the curvature of the first optical member (1) and establishes a minimum optical power for the intraocular lens.

12. Intraocular lens, according to claim 1, characterized in that the second optical member (2) and the first optical member (1) are coupled to each other by a mechanical coupling system.

13. Intraocular lens, according to claim 12, characterized in that:
the mechanical coupling system comprises a plurality of flexible flanges (3c) emerging from the first optical member (1) adjacent to a first one (2b) of the curved sides (2a, 2b) of the second optical member (2), and holding portions of a peripheral region of a second one (2a) of the curved sides (2a, 2b) of the second optical member (2) which is opposed to the first curved side (2b);
each of the flexible flanges (3c) comprises a bent free end portion (3) contacting the second curved surface (2a) of the second optical member (2) and pressing the first side (2b) of the second optical member (2) against the first surface (1a) of the first optical member (1);
bent free end portions (3) slide on the curved anterior side (2a) when the first optical member (1) deforms in response to the traction forces received.

14. Intraocular lens, according to claim 1, characterized in the second optical member is undetachably joined to the first optical member (1).

\* \* \* \* \*